United States Patent [19]
He et al.

[11] Patent Number: 6,031,097
[45] Date of Patent: Feb. 29, 2000

[54] 1-(N-(ARYLALKYLAMINOALKYL) AMINOISOQUINOLINES; A NEW CLASS OF DOPAMINE RECEPTOR SUBTYPE SPECIFIC LIGANDS

[75] Inventors: Xiao-shu He; Brian de Costa, both of Branford; Jan W.F. Wasley, Guilford, all of Conn.

[73] Assignee: Neurogen Corporation, Branford, Conn.

[21] Appl. No.: 09/179,052

[22] Filed: Oct. 26, 1998

Related U.S. Application Data

[60] Provisional application No. 60/063,512, Oct. 27, 1997.

[51] Int. Cl.⁷ .................. C07D 401/12; C07D 401/14
[52] U.S. Cl. .................. 544/295; 544/333; 544/363; 544/364; 544/373; 546/143; 548/471
[58] Field of Search ................. 544/363, 295

[56] References Cited

U.S. PATENT DOCUMENTS

| | | | |
|---|---|---|---|
| 5,149,815 | 9/1992 | Sabb | 546/163 |
| 5,602,168 | 2/1997 | He et al. | 514/416 |
| 5,656,632 | 8/1997 | He et al. | 514/253 |
| 5,744,472 | 4/1998 | He et al. | 514/253 |

*Primary Examiner*—Emily Bernhardt
*Attorney, Agent, or Firm*—McDonnell Boehnen Hulbert & Berghoff; Steven J. Sarussi

[57] ABSTRACT

Disclosed are compounds of the formula

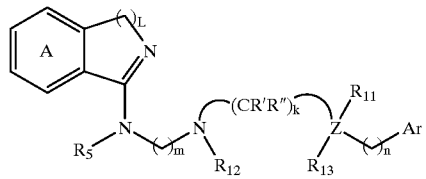

or the pharmaceutically acceptable salts thereof wherein
the 6-membered A ring may be optionally substituted with up to four groups independently selected from halogen, hydroxy, lower alkyl, or lower alkoxy;
Ar represents optionally substituted aryl or heteroaryl
Z represents carbon or nitrogen provided that
where Z is carbon, $R_{11}$ represents hydrogen, halogen, hydroxy, lower alkyl, or lower
alkoxy, or phenyl optionally substituted with one or two groups selected from hydrogen, halogen, hydroxy, lower alkyl, or lower alkoxy; and
where Z is nitrogen, $R_{11}$ represents an electron pair;
$R_5$ is hydrogen or lower alkyl;
L and m represent integers;
n is 0, or an integer;
$R_{12}$ and $R_{13}$ independently represent lower alkyl; or together may together form an optionally substituted 5–11 membered ring with the nitrogen atoms to which they are bonded; CR'R" represents a methylene group optionally substituted with lower alkyl; and
k is an integer of from 1 to 3,
which compounds are useful in treating various neuropsychochological disorders including, for example, schizophrenia, dementia, depression, anxiety, Parkinson-like motor disorders and motion disorders related to the use of neuroleptic agents.

26 Claims, No Drawings

1-(N-(ARYLALKYLAMINOALKYL) AMINOISOQUINOLINES; A NEW CLASS OF DOPAMINE RECEPTOR SUBTYPE SPECIFIC LIGANDS

This application claims the benefit of U.S. Provisional Application No. 60/063,512, filed Oct. 27, 1997.

BACKGROUND OF THE INVENTION

1. Field of the Invention

This invention relates to compounds which selectively bind to brain dopamine receptor subtypes. More specifically, it relates to 1-(N'-(arylalkylaminoalkyl)) aminoisoquinolines and to pharmaceutical compositions comprising such compounds. It further relates to the use of such compounds in treating various neuropsychochological disorders.

2. Description of the Related Art

Schizophrenia or psychosis is a term used to describe a group of illnesses of unknown origin which affect approximately 2.5 million people in the United States. These disorders of the brain are characterized by a variety of symptoms which are classified as positive symptoms (disordered thought, hallucinations and delusions) and negative symptoms (social withdrawal and unresponsiveness). These disorders have an age of onset in adolescence or early adulthood and persist for many years. The disorders tend to become more severe during the patient's lifetime and can result in prolonged institutionalization. Within the United States of America, approximately 40% of all hospitalized psychiatric patients suffer from schizophrenia.

During the 1950's physicians demonstrated that they could successfully treat psychotic (schizophrenic) patients with medications called neuroleptics. This classification of antipsychotic medication was based largely on the activating (neuroleptic) properties of the nervous system by these drugs. Subsequently, neuroleptic agents were shown to increase the concentrations of dopamine metabolites in the brain. This finding suggested that altered neuronal firing of the dopamine system contributed in some way to the aberrant behavior observed in schizophrenic patients. Additional evidence indicated that dopamine could increase the activity of adenylate cyclase in the corpus striatum, an effect reversed by neuroleptic agents. Thus, cumulative evidence from these and later experiments strongly suggested that the neurotransmitter dopamine was involved in schizophrenia.

One of the major actions of antipsychotic medication is the blockade of dopamine receptors in brain. Several dopamine systems appear to exist in the brain and at least five classes of dopamine receptors appear to mediate the actions of this transmitter. These dopamine receptors differ in their pharmacological specificity and were originally classified on the basis of their ability to bind various dopaminergic ligands.

The butyrophenones are a class of drugs containing many potent antipsychotic drugs. Perhaps the most prominent member of this class of compounds is the antipsychotic drug haloperidol (chemical name). Haloperidol binds relatively weakly at the major dopamine receptor subtype which activates adenylate cyclase (commonly classified as the $D_1$ dopamine receptor). In contrast, haloperidol displayed binding affinity at a dopamine receptor subtype which suppressed the activity of adenylate cyclase (commonly classified as $D_2$ receptors) in the subnanomolar range.

Recently, three additional dopamine receptor subtypes have been identified using the often congruent sciences of receptor pharmacology and molecular biology. These new dopamine receptors have been labeled as $D_3$, $D_4$, and $D_5$. The $D_3$ and $D_4$ subtypes are pharmacologically related to the $D_2$ receptor via their ability to suppress the activity of adenylate cyclase. Conversely, the $D_5$ receptor is classified as a "$D_1$-like" dopamine subtype through its ability to stimulate cyclase activity.

Recently, a new group of drugs (such as sulpiride and clozapine) have been developed with a lesser incidence of extrapyramidal side effects (EPS) than classical neuroleptics. In addition, there is some indication that they may be more beneficial in treating negative symptoms in some patients. Since all $D_2$ blockers do not possess a similar profile, hypotheses underlying the differences have been investigated. Major differences have been detected in the anticholinergic actions of these drugs. It has also been suggested that the dopamine receptors in motor areas may differ from those in the limbic areas which are thought to mediate the antipsychotic responses. The existence of the $D_3$, $D_4$ and $D_5$ and other as yet undiscovered dopamine receptors may contribute to this profile. Some of the atypical compounds possess similar activity at $D_2$, $D_3$ and $D_4$ receptors.

Using molecular biological techniques it has been possible to clone cDNAs coding for each of the pharmacologically defined receptors. There are at least two forms of $D_1$ which have been identified as $D_1$ and $D_5$, and two forms of $D_2$, identified now as $D_2$ and $D_4$ dopamine receptors. In addition, there is at least one form of $D_3$ dopamine receptor.

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Van Tol, H. H. et al., Nature, 1991, 350, 610). Its unique localization in limbic brain areas and its differential recognition of various antipsychotics suggest that $D_4$ receptor plays a major role in the etiology of schizophrenia. Thus, selective $D_4$ antagonists are considered effective antipsychotics free from the neurological side effects displayed by conventional neuroleptics.

U.S. Pat. Nos. 5,602,168: 5,602,168 and 5,656,632, describe aminoisoindoles useful in treating neuropsychological disorders.

SUMMARY OF THE INVENTION

This invention provides novel compounds that interact with dopamine receptor subtypes.

The invention also provides pharmaceutical compositions comprising compounds of Formula 1A. The invention also provides compounds useful in treating affective disorders such as schizophrenia and depression as well as certain movement disorders such as Parkinsonism. Furthermore, compounds of this invention are useful in treating the extrapyramidyl side effects associated with the use of conventional neuroleptic agents. Since particularly dopamine $D_3$ and $D_4$ receptor subtypes are concentrated in the limbic system (Taubes, Science 265 (1994) 1034) which controls cognition and emotion, compounds that interact with these receptors have utility in the treatment of cognitive disorders. Such disorders include the cognitive deficits which are a significant component of the negative symptoms (social withdrawal and unresponsiveness) of schizophrenia. Other disorders involving memory impairment or attention deficit disorders can also be treated with the compounds of this invention which interact specifically with dopamine $D_3$ and/or $D_4$ receptor subtypes. Accordingly, a broad aspect of the invention is directed to a compounds of Formula 1A

1A where
the 6-membered A ring is optionally substituted with up to four groups independently selected from halogen, hydroxy, lower alkyl, or lower alkoxy;
Ar represents optionally substituted aryl or heteroaryl
Z represents carbon or nitrogen provided that
  where Z is carbon, $R_{11}$ represents hydrogen, halogen, hydroxy, lower alkyl, or lower
  alkoxy, or phenyl optionally substituted with one or two groups selected from
  hydrogen, halogen, hydroxy, lower alkyl, or lower alkoxy; and
  where Z is nitrogen, $R_{11}$ represents an electron pair;
$R_5$ is hydrogen or lower alkyl;
L is an integer of from 1–4;
m is an integer of from 2–5;
n is 0, or an integer of from 1–4;
$R_{12}$ and $R_{13}$ independently represent lower alkyl; or together may represent $(CR_xR_y)_s$ where s is an integer of from 1–6 and $R_x$ and $R_y$ independently represent hydrogen or lower alkyl;
CR'R" represents a methylene group optionally substituted with lower alkyl; and
k is an integer of from 1 to 3.

In another aspect, the invention provides compounds of Formula 1B

1B or the pharmaceutically acceptable addition salts thereof wherein:
$R_1$, $R_2$, $R_3$, $R_4$ and $R_5$ independently represent hydrogen, halogen, hydroxy, alkyl, alkoxy, alkylthio, amino, monoalkylamino, dialkylamino, cyano, nitro, trifluoromethyl or trifluoromethoxy;
$R_6$ is hydrogen or $C_1$–$C_6$ alkyl, more preferably $R_6$ is hydrogen, methyl or ethyl;
W is carbon or nitrogen;
A represents an alkylene group of 2 to 5 carbon atoms optionally substituted with one or more alkyl groups having from 1 to 4 carbon atoms;
m is 0 or an integer of from 1 to 2; and
Ar represents optionally substituted aryl or heteroaryl.

Thus, the compounds of Formula 1A can be used in the treatment of various neuropsychochological disorders including, for example, schizophrenia, dementia, depression, anxiety, Parkinson-like motor disorders and motion disorders related to the use of neuroleptic agents.

Furthermore, compounds of this invention may be useful in treatment of depression, memory-impairment or Alzheimer's disease by modulation of $D_4$ receptors which selectively exist in limbic area know to control emotion and cognitive funsions. The interaction of 1-aminoalkylaminoisoquinolines with dopamine receptor subtypes is described. This interaction results in the pharmacological activities of these compounds.

DETAILED DESCRIPTION OF THE INVENTION

The novel compounds encompassed by the instant invention can be described by general formula 1A-1:

1A-1 wherein:
$R_1$, $R_2$, $R_3$, $R_4$ and $R_7$, $R_8$ and $R_9$ are the same or different and represent hydrogen, halogen, hydroxy, lower alkyl, or lower alkoxy;
X represents carbon or nitrogen provided that
  where X carbon, $R_6$ represents hydrogen, halogen, hydroxy, lower alkyl having 1–6 carbon atoms, or lower alkoxy; and
  where X is nitrogen, $R_6$ represents an electron pair;
Y represents carbon or nitrogen provided that
  where Y is carbon, $R_{10}$ represents hydrogen, halogen, hydroxy, lower alkyl, or lower alkoxy; and
  where Y is nitrogen, $R_{10}$ represents an electron pair;
Z represents carbon or nitrogen provided that
  where Z is carbon, $R_{11}$ represents hydrogen, halogen, hydroxy, lower alkyl, or lower alkoxy, or phenyl optionally substituted with one or two groups selected from hydrogen, halogen, hydroxy, lower alkyl, or lower alkoxy; and
  when Z is nitrogen, $R_{11}$ represents an electron pair;
$R_5$ is hydrogen or lower alkyl;
L is an integer of from 1–4;
m is an integer of from 2–5;
n is 0, or an integer of from 1–4;
$R_{12}$ and $R_{13}$ independently represent lower alkyl; or
$R_{12}$ and $R_{13}$ taken together may represent $(CR_xR_y)_s$ where s is an integer of from 1–6 and $R_x$ and $R_y$ independently represent hydrogen or lower alkyl;
$R_7$ and $R_8$ together may represent a benzo ring optionally substituted with up to four substitutents selected from hydrogen, halogen, hydroxy, lower alkyl, or lower alkoxy; and
$R_{14}$, $R_{15}$, $R_{16}$ and $R_{17}$ are the same or different and represent hydrogen or lower alkyl.

The present invention also encompasses compounds of Formula 2:

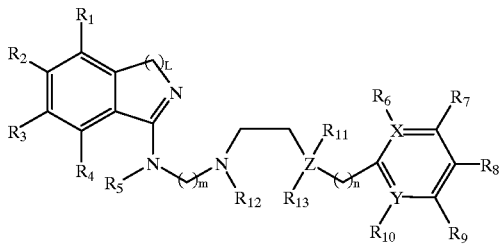

wherein:
$R_1$, $R_2$, $R_3$, $R_4$ and $R_7$, $R_8$ and $R_9$ are the same or different and represent hydrogen, halogen, hydroxy, lower alkyl, or lower alkoxy;
X represents carbon or nitrogen provided that
  where X is carbon, $R_6$ represents hydrogen, halogen, hydroxy, lower alkyl having 1–6 carbon atoms, or lower alkoxy; and
  where X is nitrogen, $R_6$ represents an electron pair;
Y represents carbon or nitrogen provided that
  where Y is carbon, $R_{10}$ represents hydrogen, halogen, hydroxy, lower alkyl, or lower alkoxy; and
  where Y is nitrogen, $R_{10}$ represents an electron pair;
Z represents carbon or nitrogen provided that
  where Z is carbon, $R_{11}$ represents hydrogen, halogen, hydroxy, lower alkyl, or lower alkoxy, or phenyl optionally substituted with one or two groups selected from hydrogen, halogen, hydroxy, lower alkyl, or lower alkoxy; and
  When Z is nitrogen, $R_{11}$ represents an electron pair;
$R_5$ is hydrogen or lower alkyl;
L is an integer of from 1–4;
m is an integer of from 2–5;
n is 0, or an integer of from 1–4;
$R_{12}$ and $R_{13}$ independently represent lower alkyl; or
$R_{12}$ and $R_{13}$ taken together represent $(CH_2)_s$ where s is an integer of from 1–6;
$R_7$ and $R_8$ together may represent a benzo ring optionally substituted with up to four substitutents selected from hydrogen, halogen, hydroxy, lower alkyl, or lower alkoxy.

The present invention further encompasses compounds of Formula 3:

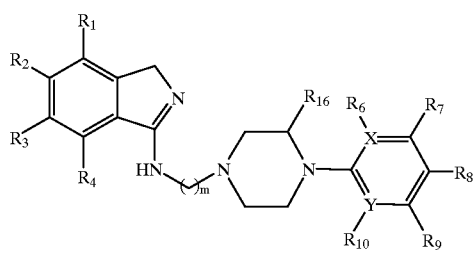

wherein:
$R_1$, $R_2$, $R_3$, $R_4$ and $R_7$, $R_8$ and $R_9$ are the same or different and represent hydrogen, halogen, hydroxy, lower alkyl, or lower alkoxy;
$R_{16}$ represents hydrogen or lower alkyl;
X represents carbon or nitrogen provided that
  where X carbon, $R_6$ represents hydrogen, halogen, hydroxy, lower alkyl having 1–6 carbon atoms, or lower alkoxy; and
  where X is nitrogen, $R_6$ represents an electron pair;
Y represents carbon or nitrogen provided that
  where Y is carbon, $R_{10}$ represents hydrogen, halogen, hydroxy, lower alkyl, or lower alkoxy; and
  where Y is nitrogen, $R_{10}$ represents an electron pair;
m is an integer of from 2–5;
$R_7$ and $R_8$ together optionally represent a benzo ring optionally substituted with up to four substitutents selected from hydrogen, halogen, hydroxy, lower alkyl, or lower alkoxy.

Preferred compounds of formula 3 are those where m is 2, 3 or 4. Particularly preferred compounds of Formula 3 are those where m is 2 or 3; $R_1$, $R_2$, $R_3$, $R_4$ are hydrogen; $R_7$ and $R_9$ are hydrogen and $R_8$ is hydrogen, hydroxy, halogen or alkoxy. More particularly preferred compounds of Formula 3 are those where m is 2 or 3; $R_1$, $R_2$, $R_3$, $R_4$ are hydrogen; $R_{16}$ is hydrogen or methyl; $R_7$ and $R_9$ are hydrogen; and $R_8$ is hydrogen, hydroxy or methoxy. Still other preferred compounds of formula 3 are those where m is 2 or 3; X and Y independently represent methylene optionally substituted with lower alkyl, preferably methyl; $R_1$, $R_2$, $R_3$, $R_4$ are hydrogen; $R_{16}$ is hydrogen or methyl; $R_7$ and $R_9$ are hydrogen and $R_8$ is hydrogen, hydroxy or methoxy.

The present invention also encompasses compounds of Formula 4:

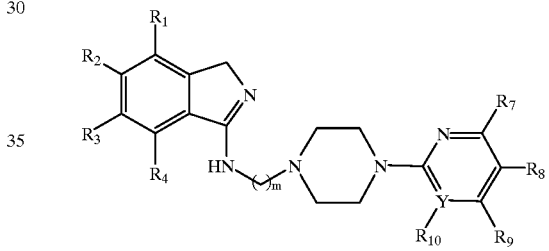

wherein:
$R_1$, $R_2$, $R_3$, $R_4$ and $R_7$, $R_8$ and $R_9$ are the same or different and represent hydrogen, halogen, hydroxy, lower alkyl, or lower alkoxy;
Y represents carbon or nitrogen provided that
  where Y is carbon, $R_{10}$ represents hydrogen, halogen, hydroxy, lower alkyl, or lower alkoxy; and
  where Y is nitrogen, $R_{10}$ represents an electron pair;
m is an integer of from 2–5; and
$R_7$ and $R_8$ together may represent a benzo ring optionally substituted with up to four substitutents selected from hydrogen, halogen, hydroxy, lower alkyl, or lower alkoxy.

Preferred compounds of formula 4 are those where m is 2, 3 or 4. Particularly preferred compounds of Formula 4 are those where m is 2 or 3; and $R_1$, $R_2$, $R_3$, $R_4$ are hydrogen; $R_7$ and $R_9$ are hydrogen; and $R_8$ is hydrogen, hydroxy, halogen or alkoxy. More particularly preferred compounds of Formula 4 are those where m is 2 or 3; and $R_1$, $R_2$, $R_3$, $R_4$ are hydrogen; $R_7$ and $R_9$ are hydrogen; and $R_8$ is hydrogen, hydroxy or methoxy.

The present invention also encompasses compounds of Formula 5:

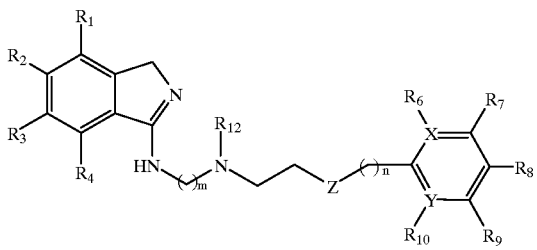

wherein:
R$_1$, R$_2$, R$_3$, R$_4$ and R$_7$, R$_8$ and R$_9$ are the same or different and represent hydrogen, halogen, hydroxy, lower alkyl, or lower alkoxy;
X represents carbon or nitrogen provided that
  where X carbon, R$_6$ represents hydrogen, halogen, hydroxy, lower alkyl having 1–6 carbon atoms, or lower alkoxy; and
  where X is nitrogen, R$_6$ represents an electron pair;
Y represents carbon or nitrogen provided that
  where Y is carbon, R$_{10}$ represents hydrogen, halogen, hydroxy, lower alkyl, or lower alkoxy; and
  where Y is nitrogen, R$_{10}$ represents an electron pair;
Z represents CH$_2$ or nitrogen;
m is an integer of from 2–5;
n is 0, or an integer of from 1–4;
R$_{12}$ represents hydrogen or lower alkyl; and
R$_7$ and R$_8$ together optionally represent a benzo ring optionally substituted with up to four substitutents selected from hydrogen, halogen, hydroxy, lower alkyl, or lower alkoxy.

Preferred compounds of formula 5 are those where m is 2, 3 or 4 and n is 0. Particularly preferred compounds of Formula 5 are those where R$_{12}$ is hydrogen or alkyl; m is 2, n is 0; Z is CH$_2$; R$_1$, R$_2$, R$_3$, R$_4$ are hydrogen; R$_7$ and R$_9$ are hydrogen; and R$_8$ is hydrogen, hydroxy, halogen or alkoxy. More particularly preferred compounds of Formula 5 are those where R$_{12}$ is hydrogen or methyl; m is 2; n is 0; Z is CH$_2$; and R$_1$, R$_2$, R$_3$, R$_4$ are hydrogen; R$_7$ and R$_9$ are hydrogen; and R$_8$ is hydrogen, hydroxy or methoxy.

In addition, the present invention provides compounds of Formula 6:

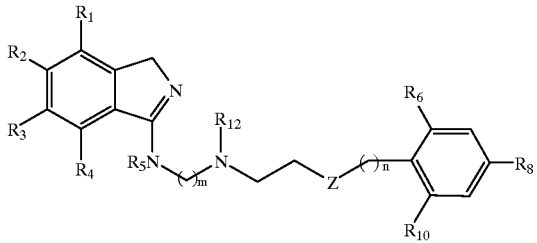

wherein:
R$_1$, R$_2$, R$_3$, R$_4$ and R$_8$ are the same or different and represent hydrogen, halogen, hydroxy, lower alkyl, or lower alkoxy;
R$_6$ and R$_{10}$ independently represent hydrogen, halogen, hydroxy, lower alkyl, or lower alkoxy;
Z represents CH$_2$ or nitrogen;
m is an integer of from 2–5;
R$_5$ represents hydrogen or lower alkyl;
n is 0, or an integer of from 1–4; and
R$_{12}$ represents lower alkyl.

Preferred compounds of formula 6 are those where m is 2, 3 or 4 and n is 0. Particularly preferred compounds of Formula 6 are those where R$_{12}$ is hydrogen or alkyl; m is 2, n is 0; Z is CH$_2$; R$_1$, R$_2$, R$_3$, R$_4$ are hydrogen; and R$_8$ is hydrogen, hydroxy, halogen or alkoxy. More particularly preferred compounds of Formula 6 are those where R$_{12}$ is hydrogen or methyl; R$_6$ is hydrogen; R$_{10}$ is hydrogen or lower alkoxy, preferably methoxy; m is 2; n is 0; Z is CH$_2$; and R$_1$, R$_2$, R$_3$, R$_4$ are hydrogen; and R$_8$ is hydrogen, hydroxy or methoxy.

In addition, the present invention provides compounds of Formula 7:

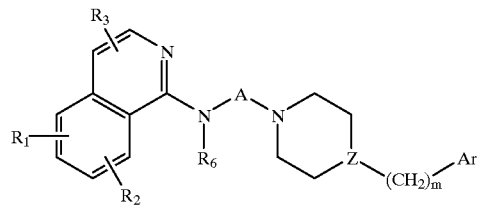

wherein:
R$_1$, R$_2$, and R$_3$ independently represent hydrogen, halogen, hydroxy, alkyl, alkoxy, alkylthio, amino, monoalkylamino, dialkylamino, cyano, nitro, trifluoromethyl or trifluoromethoxy;
R$_6$ is hydrogen or C$_1$–C$_6$ alkyl, more preferably R$_6$ is hydrogen, methyl or ethyl;
Z is carbon or nitrogen;
A represents an alkylene group of 2 to 5 carbon atoms optionally substituted with one or more alkyl groups having from 1 to 4 carbon atoms;
m is 0 or an integer of from 1 to 2; and
Ar represents aryl or heteroaryl of the formula

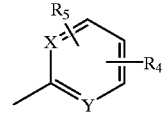

where:
  Y and Z are the same or different and represent either carbon or nitrogen; and
  R$_4$ and R$_5$ independently represent hydrogen, halogen, alkyl, alkoxy, alkylthio, hydroxy, amino, monoalkylamino, dialkylamino, cyano, nitro, trifluoromethyl or trifluoromethoxy.

The present invention also provides compounds of Formula 8:

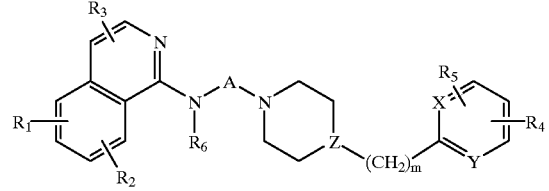

wherein:
R$_1$, R$_2$, and R$_3$ independently represent hydrogen, halogen, hydroxy, alkyl, alkoxy, alkylthio, amino, monoalkylamino, dialkylamino, cyano, nitro, trifluoromethyl or trifluoromethoxy;

$R_6$ is hydrogen or $C_1$–$C_6$ alkyl, more preferably $R_6$ is hydrogen, methyl or ethyl;

Z is carbon or nitrogen;

A represents an alkylene group of 2 to 5 carbon atoms optionally substituted with one or more alkyl groups having from 1 to 4 carbon atoms;

m is 0 or an integer of from 1 to 2;

X and Y are the same or different and represent either carbon or nitrogen; and $R_4$ and $R_5$ independently represent hydrogen, halogen, alkyl, alkoxy, alkylthio, hydroxy, amino, monoalkylamino, dialkylamino, cyano, nitro, trifluoromethyl or trifluoromethoxy.

The invention further encompasses compounds of Formula 9:

[Structure 9]

wherein:

$R_1$, $R_2$, and $R_3$ independently represent hydrogen, halogen, hydroxy, alkyl, alkoxy, alkylthio, amino, monoalkylamino, dialkylamino, cyano, nitro, trifluoromethyl or trifluoromethoxy;

$R_6$ is hydrogen or $C_1$–$C_6$ alkyl, more preferably $R_6$ is hydrogen, methyl or ethyl;

A represents an alkylene group of 2 to 5 carbon atoms optionally substituted with one or more alkyl groups having from 1 to 4 carbon atoms;

m is 0 or an integer of from 1 to 2; and

Ar represents optionally substituted aryl or heteroaryl.

In addition, the invention provides compounds of Formula 10:

[Structure 10]

wherein:

$R_1$, $R_2$, and $R_3$ independently represent hydrogen, halogen, hydroxy, alkyl, alkoxy, alkylthio, amino, monoalkylamino, dialkylamino, cyano, nitro, trifluoromethyl or trifluoromethoxy;

$R_6$ is hydrogen or $C_1$–$C_6$ alkyl, more preferably $R_6$ is hydrogen, methyl or ethyl;

A represents an alkylene group of 2 to 5 carbon atoms optionally substituted with one or more alkyl groups having from 1 to 4 carbon atoms;

m is 0 or an integer of from 1 to 2;

Y and X are the same or different and represent either carbon or nitrogen; and $R_4$ and $R_5$ independently represent hydrogen, halogen, alkyl, alkoxy, alkylthio, hydroxy, amino, monoalkylamino, dialkylamino, cyano, nitro, trifluoromethyl or trifluoromethoxy.

Preferred compounds of formula 10 are those where A is alkylene of from 2–4 carbon atoms. More preferred compounds of Formula 10 are those where A is alkylene of from 2–4 carbon atoms; $R_1$, $R_2$, and $R_3$ are hydrogen; $R_6$ is hydrogen or $C_{1-2}$ alkyl, and $R_4$ and $R_5$ independently represent hydrogen, hydroxy, halogen or alkoxy. Particularly preferred compounds of Formula 10 are those where A is alkylene of from 2–4 carbon atoms; $R_1$, $R_2$, and $R_3$ are hydrogen; $R_6$ is hydrogen or $C_{1-2}$ alkyl, Y and X are both nitrogen, and $R_4$ and $R_5$ independently represent hydrogen, hydroxy, halogen or alkoxy. Other particularly preferred compounds of Formula 10 are those where A is alkylene of from 2–4 carbon atoms; $R_1$, $R_2$, and $R_3$ are hydrogen; $R_6$ is hydrogen or $C_{1-2}$ alkyl, Y is carbon and X is nitrogen, and $R_4$ and $R_5$ independently represent hydrogen, hydroxy, halogen or alkoxy. Still other particularly preferred compounds of Formula 10 are those where A is alkylene of from 2–4 carbon atoms; $R_1$, $R_2$, and $R_3$ are hydrogen; $R_6$ is hydrogen or $C_{1-2}$ alkyl, Y and X are carbon, and $R_4$ and $R_5$ independently represent hydrogen, hydroxy, halogen or alkoxy.

Further, the present invention encompasses compounds of Formula 11:

[Structure 11]

wherein:

$R_1$, $R_2$, and $R_3$ independently represent hydrogen, halogen, hydroxy, alkyl, alkoxy, alkylthio, amino, monoalkylamino, dialkylamino, cyano, nitro, trifluoromethyl or trifluoromethoxy;

$R_6$ is hydrogen or $C_1$–$C_6$ alkyl, more preferably $R_6$ is hydrogen, methyl or ethyl;

A represents an alkylene group of 2 to 5 carbon atoms optionally substituted with one or more alkyl groups having from 1 to 4 carbon atoms;

m is 0 or an integer of from 1 to 2; and

Ar represents optionally substituted aryl or heteroaryl.

The invention further provides compounds of Formula 12:

[Structure 12]

wherein:

$R_1$, $R_2$, and $R_3$ independently represent hydrogen, halogen, hydroxy, alkyl, alkoxy, alkylthio, amino, monoalkylamino, dialkylamino, cyano, nitro, trifluoromethyl or trifluoromethoxy;

$R_6$ is hydrogen or $C_1$–$C_6$ alkyl, more preferably $R_6$ is hydrogen, methyl or ethyl;

A represents an alkylene group of 2 to 5 carbon atoms optionally substituted with one or more alkyl groups having from 1 to 4 carbon atoms;

m is 0 or an integer of from 1 to 2;

Y and X are the same or different and represent either carbon or nitrogen; and $R_4$ and $R_5$ independently represent hydrogen, halogen, alkyl, alkoxy, alkylthio, hydroxy, amino, monoalkylamino, dialkylamino, cyano, nitro, trifluoromethyl or trifluoromethoxy.

Preferred compounds of formula 12 are those where A is alkylene of from 2–4 carbon atoms. More preferred compounds of Formula 12 are those where A is alkylene of from 2–4 carbon atoms; $R_1$, $R_2$, and $R_3$ are hydrogen; $R_6$ is hydrogen or $C_{1-2}$ alkyl, and $R_4$ and $R_5$ independently represent hydrogen, hydroxy, halogen or alkoxy. Particularly preferred compounds of Formula 12 are those where A is alkylene of from 2–4 carbon atoms; $R_1$, $R_2$, and $R_3$ are hydrogen; $R_6$ is hydrogen or $C_{1-2}$ alkyl, Y and X are both nitrogen, and $R_4$ and $R_5$ independently represent hydrogen, hydroxy, halogen or alkoxy. Other particularly preferred compounds of Formula 12 are those where A is alkylene of from 2–4 carbon atoms; $R_1$, $R_2$, and $R_3$ are hydrogen; $R_6$ is hydrogen or $C_{1-2}$ alkyl, Y is carbon and X is nitrogen, and $R_4$ and $R_5$ independently represent hydrogen, hydroxy, halogen or alkoxy. Still other particularly preferred compounds of Formula 12 are those where A is alkylene of from 2–4 carbon atoms; $R_1$, $R_2$, and $R_3$ are hydrogen; $R_6$ is hydrogen or $C_{1-2}$ alkyl, Y and X are carbon, and $R_4$ and $R_5$ independently represent hydrogen, hydroxy, halogen or alkoxy.

Representative Ar groups of formula 1B above include the following:

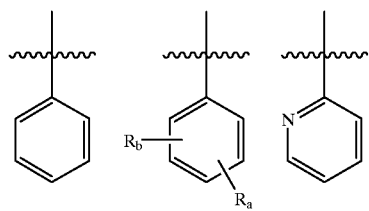

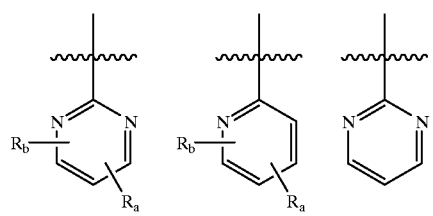

In the above Formula 1B Ar groups, the following definitions apply:

$R_a$ is halogen, alkyl, hydroxy, or alkoxy; and $R_b$ represents hydrogen or alkyl.

In those formulas where more than one of the same substituent appears, e.g., alkyl, those substituents are the same or different.

Preferred Ar groups of formula 1B above include the following:

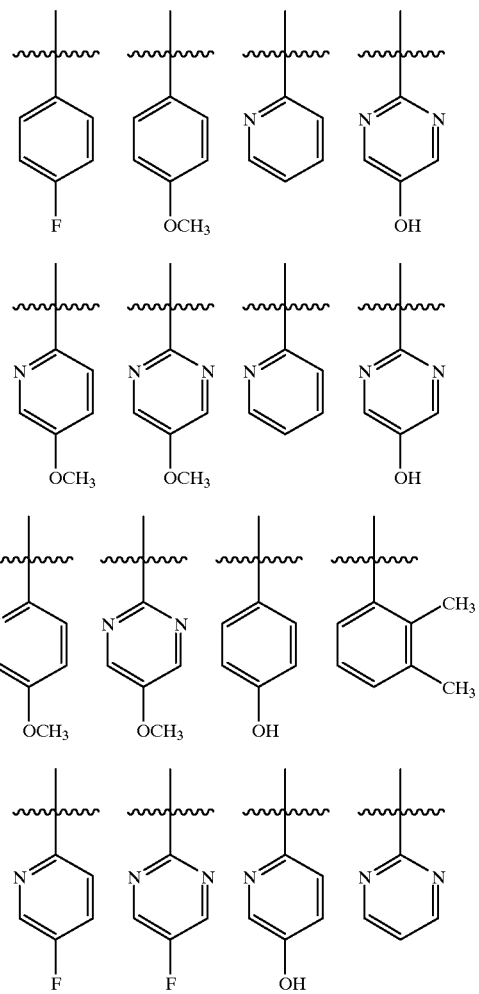

Representative

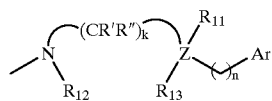

groups of formula 1A above include the following:

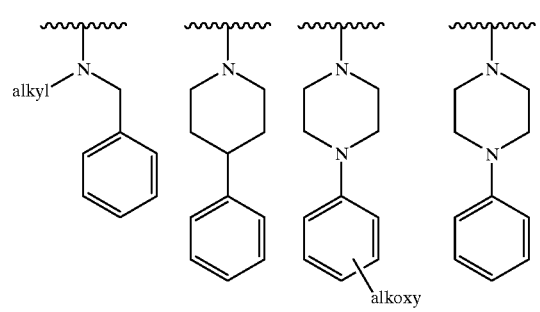

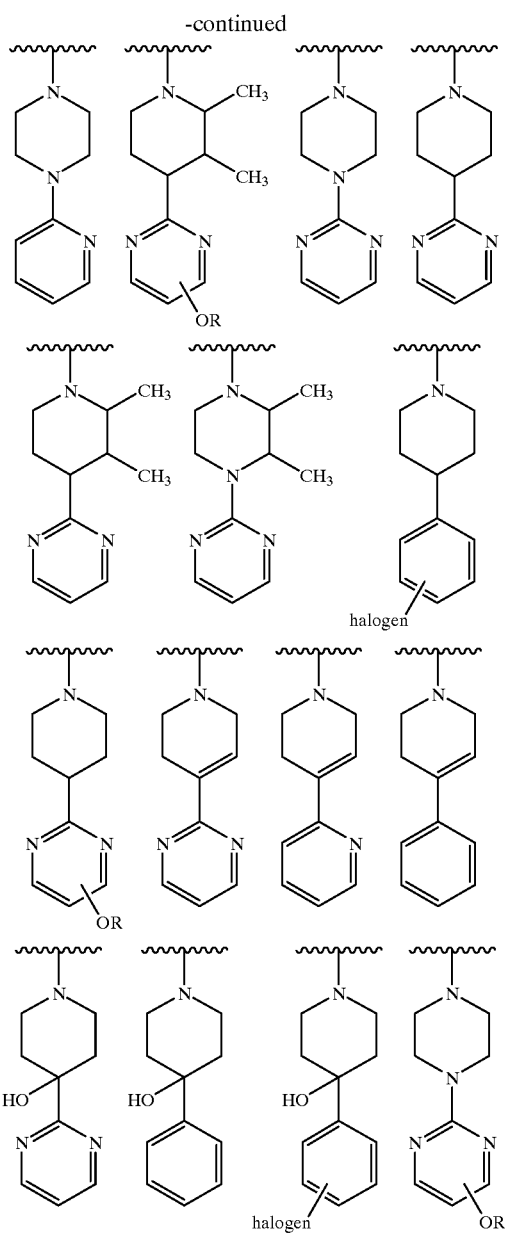

Preferred

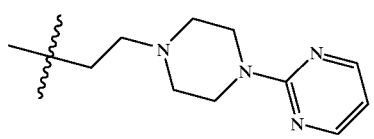

groups of formula 1A above include the following:

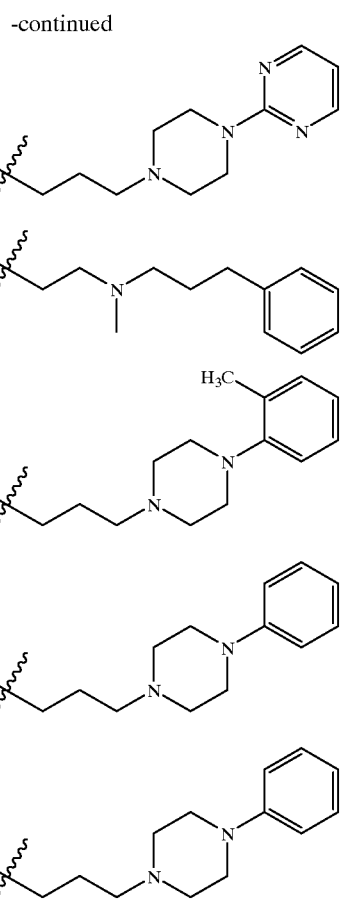

In the above preferred groups, OR represents hydroxy or alkoxy.

Representative compounds of the present invention, which are encompassed by Formula 1, include, but are not limited to the compounds shown below in Table 1 and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula 1. Those skilled in the art will recognize various synthetic methodologies which can be employed to prepare non-toxic pharmaceutically acceptable addition salts and acylated prodrugs of the compounds encompassed by Formula 1.

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By "alkyl" and "lower alkyl" is meant straight and branched chain alkyl groups having from 1–6 carbon atoms.

In mono- and dialkylamino groups as used herein, the alkyl groups are independently $C_1$–$C_6$ alkyl groups.

By "lower alkoxy" and "alkoxy" is meant straight and branched chain alkoxy groups having from 1–6 carbon atoms.

By "alkylthio" is meant groups of the formula —SR where R is $C_1$–$C_6$ alkyl.

By "heteroaryl" is meant 5, 6, or 7 membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be unsubstituted or substituted with e.g., halogen, lower alkyl, lower alkoxy, lower alkylthio, trifluoromethyl, lower acyloxy, aryl, heteroaryl, and hydroxy.

By halogen is meant fluorine, chlorine, bromine and iodine.

By alkylsulfonyl is meant a sulfonyl group substituted with a lower alkyl group.

By arylalkylsulfonyl is meant a sulfonyl group substituted with an arylalkyl group.

By aminosulfonyl is meant a sulfonyl group substituted with an amino group.

By alkylaminosulfonyl is meant a sulfonyl group substituted with a lower alkylamino, or di-lower alkylamino group.

Representative examples of bridged 4-phenyl-2-aminomethylimidazoles according to the invention are shown in Table 1 below.

TABLE 1[1]

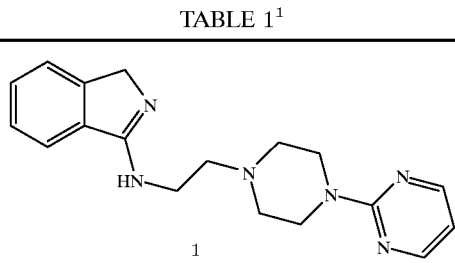

1

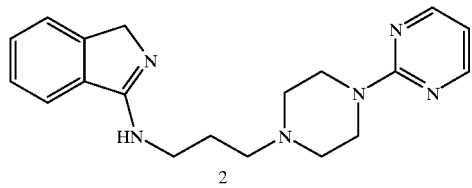

2

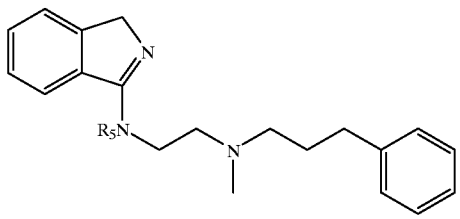

3 $R_5$ = H
4 $R_5$ = $CH_3$

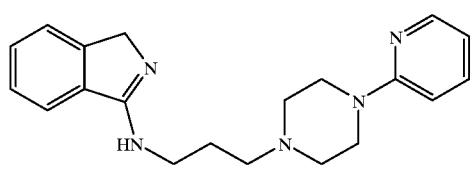

5

TABLE 1[1]-continued

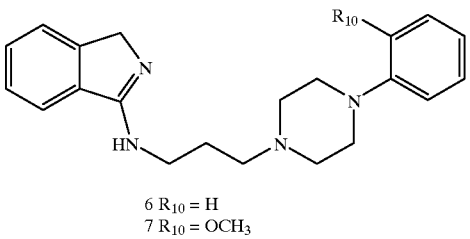

6 $R_{10}$ = H
7 $R_{10}$ = $OCH_3$

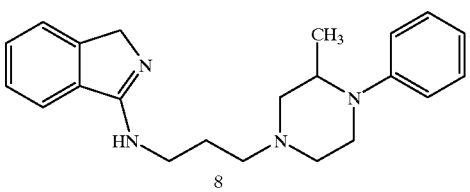

8

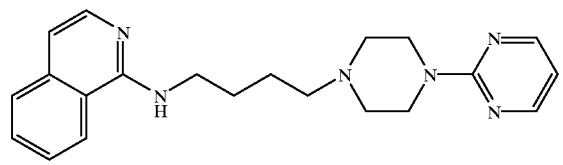

9

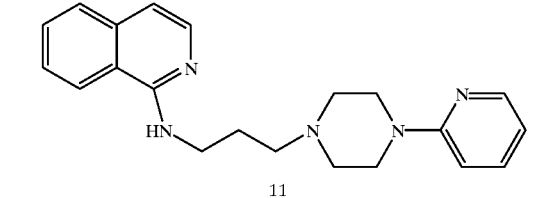

10

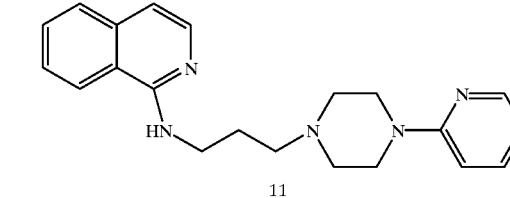

11

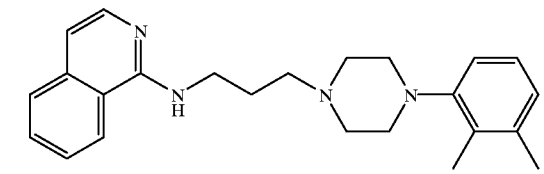

12

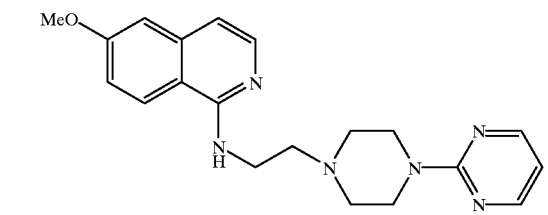

13

TABLE 1-continued

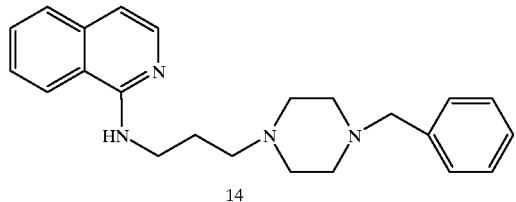

14

The number below each compound is its compound number.

The pharmaceutical utility of compounds of this invention are indicated by the following assays for dopamine receptor subtype affinity.

Assay for $D_2$ and $D_3$ Receptor Binding Activity

Pellets of COS cells containing recombinantly produced $D_2$ or $D_3$ receptors from African Green monkey were used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 mM spiperone; without further additions, nonspecific binding is less than 20% of total binding. The binding characteristics of examples of this patent for the $D_2$ and $D_3$ receptor subtypes are shown in Table 2 for Rat Striatal Homogenates.

TABLE 2

| Compound Number[1] | $D_2$ $K_i$ (mM) | D3 $K_i$ (mM) |
| --- | --- | --- |
| 1 | 2.380 | >100 |
| 2 | 1.420 | >100 |
| 3 | 1.937 | >100 |

[1]Compound numbers relate to compounds shown in Table 1 above.

Assay for $D_4$ Receptor Binding Activity

Clonal cell lines expressing the human dopamine $D_4$ receptor subtype were harvested in PBS and the cells centrifuged and the pellets stored at −80° C. until used in the binding assay. The pellets were resuspended and the cells lysed at 4° C. in 50 mM Tris pH 7.4 buffer containing 120 mM NaCl, 1 mM EDTA and 5 mM $MgCl_2$. The homogenate is centrifuged at 48000×g for 10 minutes at 4° C. The resulting pellet is resuspended in fresh buffer and centrifuged again. After resuspension of the pellet in fresh buffer a 100 ml aliquot is removed for protein determination. The remaining homogenate is centrifuged as above, the supernatant removed and the pellet stored at 4° C. until needed at which time it is resuspended to a final concentration of 625 mg/ml (250 mg per sample) with 50 mM Tris buffer (pH 7.4) and 120 mM NaCl just prior to use. Incubations were carried out for 60 minutes at 25° C. in the presence of 0.1 nM [$^3$H] YM-09151-2. The incubation was terminated by rapid filtration through Whatman GF/C filters and rinsed with 2×4 ml washes of chilled 50 mM Tris (pH 7.4) and 120 mM NaCl. Non-specific binding was determined with 1 mM spiperone and radioactivity determined by counting in an LKB beta counter. Binding parameters were determined by non-linear least squares regression analysis, from which the inhibition constant Ki could be calculated for each test compound. The binding characteristics of some examples of this invention are shown in Table 3 for the dopamine $D_4$ binding assay. In general, compounds of the accompanying Examples were tested in the above assay, and all were found to possess a Ki value for the displacement of [$^3$H]YM-09151-2 from the human dopamine $D_4$ receptor subtype of below 500 nM. Some specific data is indicated in Table 3.

TABLE 3

| Compound Number[1] | $K_i$ (mM) |
| --- | --- |
| 1 | 0.012 |
| 2 | 0.070 |
| 3 | 0.100 |

Compound numbers relate to compounds shown in Table 1 above.

Assay for $D_2$ and $D_4$ Receptor Binding Activity

Pellets of COS cells containing recombinantly produced $D_2$ or $D_4$ receptors from African Green monkey were used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 mM spiperone; without further additions, nonspecific binding is less than 20% of total binding. The binding characteristics of examples of this patent for the $D_2$ and $D_4$ receptor subtypes are shown in Table 1 for rat striatal homogenates.

TABLE 4

| Compound Number | $D_4$ $K_i$ (nM) | $D_2$ $K_i$ (nM) |
| --- | --- | --- |
| 9 | 13 | 1495 |
| 10 | 2 | 773 |

Compound number relate to compounds shown in Table 1 above.

The compounds of general Formulas 1 may be administered orally, topically, parenterally, by incubation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula 1 and a pharmaceutically acceptable carrier. One or more compounds of general Formula 1 may be present in association with one or more non-toxic pharmaceutically acceptable carriers and/or diluents and/or adjuvants and if desired other active ingredients. The pharmaceutical compositions containing compounds of general Formula 1 may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of general Formula 1 may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula 1 may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The compounds of the invention may be prepared by the reactions shown below in Scheme 1. Those having skill in the art will recognize that the starting materials may be varied and additional steps employed to produce other compounds encompassed by the present invention.

SCHEME 1
Preparation of 1-amino substituted isoindoles

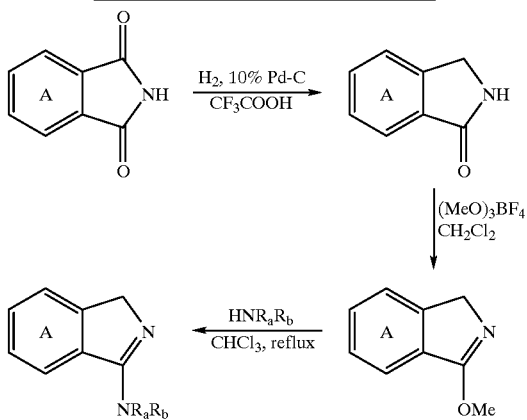

where the A ring is as defined above and $NR_aR_b$ represents the group

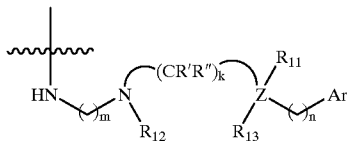

wherein CR'R", k, $R_{11}$, $R_{12}$, $R_{13}$, Ar, and m and n are as defined above.

PREPARATION OF 1-AMINOALKYLAMINOISOQUINOLINES

A compound of Formula I, or a pharmaceutically acceptable acid addition salt thereof may be prepared according to the Reaction Scheme 2.

Reaction Scheme 2

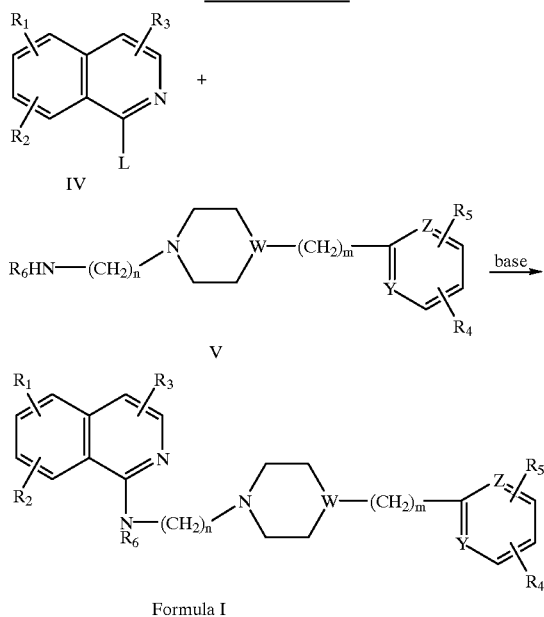

Formula I wherein $R_1$, $R_2$, $R_3$, $R_4$, $R_5$, $R_6$, n, m, W, Y and Z are as defined above for Formula 1B.

As shown, an isoquinoline of general structure IV, possessing an appropriate leaving group L at the 1 position, may be reacted with a primary or secondary amine of general structure V in the presence of a base to afford a compound of Formula I as the desired product.

Where they are not commercially available, the compounds of general structure IV may be prepared by procedures analogous to those described in the literature. Compounds of general structure V are either known or capable of being prepared by the methods known in the art. Those having skill in the art will recognize that the starting materials may be varied and additional steps employed to produce compounds encompassed by the present invention.

The invention is further illustrated by the following examples which are not to be construed as limiting the invention in scope or spirit to the specific procedures and compounds described therein.

EXAMPLE 1

To a solution of trimethyloxonium tetrafluoroborate (2.20 g, 14.9 mmol) in ($CH_2Cl_2$, 20 mL) was added a solution of phthalimidine (1.8 g, 13.5 mmol) in $CH_2Cl_2$ (20 mL) and the solution was stirred for 24 h. The solvent was evaporated in vacuo and the residue was dissolved in chloroform (80 mL). To this solution was added 1-(aminoethyl)-4-(2-pyrimidinyl)piperazine (2.08 g, 9.0 mmol) followed by triethylamine (5 mL). The solution was boiled under reflux overnight and then the solvent was evaporated in vacuo to afford a semisolid residue. The residue was dissolved in water (100 mL) and extracted with ethyl acetate (3×100 mL) to remove unreacted phthalimidine and primary amine. The aqueous solution was adjusted to about 20% NaOH by slow addition of aqueous 50% NaOH and then extracted with chloroform (2×100 mL). The combined chloroform extracts were dried ($K_2CO_3$) and evaporated to give 1 as a pale yellow oil (2.9 g, quantitative). The hydrobromide salt was crystallized from hot ethanol.

EXAMPLE 2

To a solution of trimethyloxonium tetrafluoroborate (1.10 g, 7.45 mmol) in ($CH_2C_2$, 10 mL) was added a solution of phthalimidine (0.9 g, 6.75 mmol) in $CH_2Cl_2$ (10 mL) and the solution was stirred for 24 h. The solvent was evaporated in vacuo and the residue was dissolved in chloroform (40 mL). To this solution was added 3-(aminopropyl)-4-(2-pyrimidinyl)piperazine (1.1 g, 4.5 mmol) followed by triethylamine (5 mL). The solution was boiled under reflux overnight and then the solvent was evaporated in vacuo to afford a semisolid residue. The residue was dissolved in water (50 mL) and extracted with ethyl acetate (3×50 mL) to remove unreacted phthalimidine and primary amine. The aqueous solution was adjusted to about 20% NaOH by slow addition of aqueous 50% NaOH and then extracted with chloroform (2×50 mL). The combined chloroform extracts were dried ($K_2CO_3$) and evaporated to give 2 as a pale yellow oil (0.75 g, 38%). The hydrobromide salt crystallized from hot ethanol: mp 149–150° C.; base $^1$H-NMR (CDCl3) 8.38 (d, 2H), 7.3–7.5 (m, 5H), 6.55 (t, 1H), 4.62 (s, 2H), 3.9 (m, 4H), 3.63 (m, 2H), 2.63 (m, 6H), 1.8 (m, 2H).

EXAMPLE 3

The following compounds are prepared essentially according to the procedures set forth above in Examples 1 and 2.

(a) 1-(N-[2-{N'-(3-phenylpropyl)-N'-methyl}-aminoethyl])aminoisoindole dioxolate, 3, m.p. 175–177° C.

(b) 1-(N-[2-{N'-(3-phenylpropyl)-N'-methyl}-aminoethyl]-N-methyl])aminoisoindole, 4.

(c) 1-(N-[3-{1-(4-(2-pyridyl)piperazinyl)}propylamino]) aminoisoindole dihydrobromide, 5, m.p. 283–285° C. (dec.).

(d) 1-(N-[3-{1-(4-phenylpiperazinyl)}propyl]) aminoisoindole dihydrobromide, 6, m.p. 208–211° C.

(e) 1-(N-[3-{1-(4-(2-methoxyphenyl))piperazinyl}-propyl]) aminoisoindole dihydrobromide, 7, m.p. 184–185° C..

(f) 1-(N-[3-{1-(4-phenyl-3-methyl)piperazinyl}propyl]) aminoisoindole dihydrobromide, 8.

EXAMPLE 4

Preparation of 1-(5-Fluoropyrimidin-2-yl)-4-(2-aminoethyl) piperazine

A mixture of N-(2-bromoethyl)phthalimide (17.2 g, 0.068 mole), 1-(5-fluoropyrimidin-2-yl)piperazine (12.4 g, 0.068 mole) and potassium carbonate (18.8 g, 0.14 mole) in dimethyl formamide (150 mL) was heated at 80° C. for 14 hours under a nitrogen atmosphere. After cooling, the reaction mixture was poured into water (1 L) and ether. (1 L). The heterogeneous mixture was then filtered to remove solids and the layers separated. The aqueous layer was further extracted with ether (2×300 mL). The combined organic layers were dried ($Na_2SO_4$) and concentrated to provide a yellow solid (16.9 g).

The solid were refluxed under nitrogen in hydrazine hydrate (100 mL) for 3 h. After cooling the solution was poured into 30% potassium carbonate solution (50 mL) and extracted with methylene chloride. The organic extracts were dried ($Na_2SO_4$) and concentrated to give an orange semisolid (9.7 g). This material was dissolved in methanol (5 mL) and combined with a methanolic solution (10 mL) of fumaric acid (5 g). Isopropanol was added (50 mL) and the mixture was concentrated on a hot plate to a volume of 20 mL. Upon cooling the yellow crystals of fumarate salt were collected (8.72 g, m.p. 193–194° C.)

EXAMPLE 5

Preparation of 2-(1-[2-{(4-[5-Fluoropyrimidin-2-yl]) piperazin-1-yl}]ethyl)aminoquinoline (Compound 9)

A solution of 1-(5-Fluoropyrimidin-2-yl)-4-(2-aminoethyl)piperazine (500 mg) in xylene (15 mL) was treated with 1-chloroisoquinoline (430 mg) and potassium carbonate (300 mg). The mixture was refluxed under $N_2$ overnight. After cooling the solution was diluted with diethyl ether (200 mL) and washed with water (3×50 mL). The organic layer was then extracted with a aqueous solution of 10% acetic acid. The aqueous extract was then washed with ether (50 mL), basified with 50% NaOH solution and extracted with chloroform. The chloroform layer was dried ($Na_2SO_4$) and evaporated to give the product as an oil which was purified by preparative thin layer chromatography eluting with 10% methanol in chloroform. The resulting white solid was dissolved in isopropanol:ethanol (3 mL), treated with 48% HBr until acidic. The off-white crystalline hydrobromide salt was collected by filtration (0.012 g, mp 285–288° C.).

EXAMPLE 6

The following compounds are prepared essentially according to the procedures set forth above, and, in particular, the procedures of Examples 4 and 5.

(a) 1-(1-[2-{(4-Pyrimidin-2-yl)piperazin-1-yl }]ethyl) aminoisoquinoline hydrobromide (m.p. 211–214° C.)

(b) 1-(1-[3-{(4-Pyrimidin-2-yl)piperazin-1-yl}]propyl) aminoisoquinoline hydrobromide (m.p. 174–175° C.)

(c) 1-(1-[4-{(4-Pyrimidin-2-yl)piperazin-1-yl}]butyl) aminoisoquinoline hydrobromide (Compound 8, m.p. 282–284° C.)

(d) 1-(1-[2-{(4-Pyrimidin-2-yl)piperazin-1-yl}]ethyl) amino-6-methoxyisoquinoline hydrobromide (Compound 12, m.p. >200° C.)

(e) 1-(1-[3-{(4-[2-Methoxyphenyl])piperazin-1-yl}] propyl)aminoisoquinoline hydrobromide (m.p. 161–163° C.)

(f) 1-(1-[3-{(4-Pyridin-2-yl)piperazin-1-yl}]propyl) aminoisoquinoline hydrobromide (Compound 10, m.p. 277–279° C.)

(g) 1-(1-[3-{4-Phenylpiperazin-1-yl}]propyl) aminoisoquinoline hydrobromide (m.p. 250–252° C.)

(h) 1-(1-[3-{(4-[2,3-Dimethylphenyl])piperazin-1-yl}] propyl)aminoisoquinoline hydrobromide (Compound 11, m.p. 249–252° C.)

(i) 1-(1-[2-{(4-[5-Fluoropyrimidin-2-yl])piperazin-1-yl}] ethyl)aminoisoquinoline hydrobromide (Compound 9, m.p. 285–288° C.)

(j) 1-(1-[4-{(4-[5-Fluoropyrimidin-2-yl])piperazin-1-yl}] butyl)aminoisoquinoline hydrobromide (m.p. 256–259° C.)

(k) 1-(1-[4-{(4-[5-Methylpyrimidin-2-yl])piperazin-1-yl}]butyl)aminoisoquinoline hydrobromide (m.p. 117–118° C.)

(l) 1-(1-[3-{4-Benzylpiperidin-1-yl}]propyl) aminoisoquinoline hydrobromide (Compound 13, m.p. 230–232° C.)

The disclosures in this application of all articles and references, including patents, are incorporated herein by reference.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude the specification.

What is claimed is:

1. A compound of the formula:

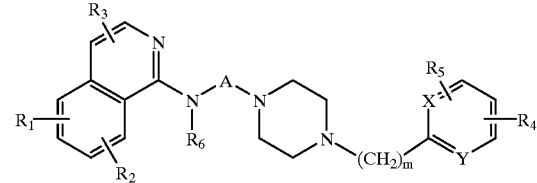

or a pharmaceutically acceptable salt thereof wherein:

$R_1$, $R_2$, and $R_3$ independently represent hydrogen, halogen, hydroxy, alkyl, alkoxy, alkylthio, amino, monoalkylamino, dialkylamino, cyano, nitro, trifluoromethyl or trifluoromethoxy;

$R_6$ is hydrogen or $C_1$–$C_6$ alkyl;

A represents an alkylene group of 2 to 5 carbon atoms optionally substituted with one or more alkyl groups having from 1 to 4 carbon atoms;

m is 0 or an integer of from 1 to 2;

Y and X are the same or different and represent either carbon or nitrogen; and

R$_4$ and R$_5$ independently represent hydrogen, halogen, alkyl, alkoxy, alkylthio, hydroxy, amino, monoalkylamino, dialkylamino, cyano, nitro, trifluoromethyl or trifluoromethoxy.

2. A compound according to claim 1, wherein A is alkylene of from 2–4 carbon atoms; R$_1$, R$_2$, and R$_3$ are hydrogen; R$_6$ is hydrogen or C$_{1-2}$ alkyl, Y is carbon and X is nitrogen, and R$_4$ and R$_5$ independently represent hydrogen, hydroxy, halogen or alkoxy.

3. A compound according to claim 1, wherein the X,Y-containing ring is selected from:

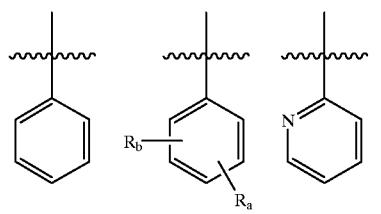

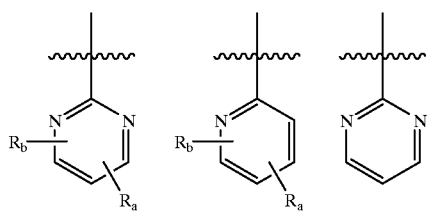

wherein:

R$_a$ is halogen, alkyl, hydroxy, or alkoxy; and

R$_b$ represents hydrogen or alkyl.

4. A compound according to claim 3, wherein Ar represents:

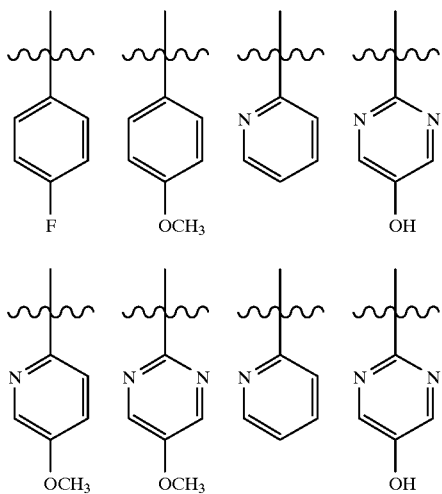

-continued

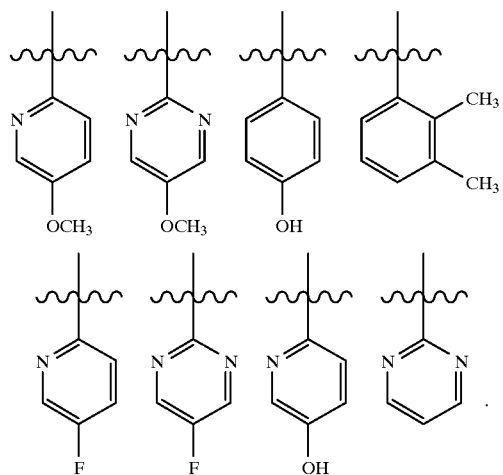

5. A compound according to claim 1, which is 1-(1-[2-{(4-Pyrimidin-2-yl)piperazin-1-yl}]ethyl)aminoisoquinoline.

6. A compound according to claim 1, which is 1-(1-[2-{(4-Pyrimidin-2-yl)piperazin-1-yl}]ethyl)aminoisoquinoline hydrobromide.

7. A compound according to claim 1, which is 1-(1-[3-{(4-Pyrimidin-2-yl)piperazin-1-yl}]propyl)aminoisoquinoline.

8. A compound according to claim 1, which is 1-(1-[3-{(4-Pyrimidin-2-yl)piperazin-1-yl}]propyl)aminoisoquinoline hydrobromide.

9. A compound according to claim 1, which is 1-(1-[4-{(4-Pyrimidin-2-yl)piperazin-1-yl}]butyl)aminoisoquinoline.

10. A compound according to claim 1, which is 1-(1-[4-{(4-Pyrimidin-2-yl)piperazin-1-yl}]butyl)aminoisoquinoline hydrobromide.

11. A compound according to claim 1, which is 1-(1-[2-{(4-Pyrimidin-2-yl)piperazin-1-yl}]ethyl)amino-6-methoxyisoquinoline.

12. A compound according to claim 1, which is 1-(1-[2-{(4-Pyrimidin-2-yl)piperazin-1-yl}]ethyl)amino-6-methoxyisoquinoline hydrobromide.

13. A compound according to claim 1, which is 1(1-[3-{(4-[2-Methoxyphenyl])piperazin-1-yl}]propyl)aminoisoquinoline.

14. A compound according to claim 1, which is 1-(1-[3-{(4-[2-Methoxyphenyl])piperazin-1-yl}]propyl)aminoisoquinoline hydrobromide.

15. A compound according to claim 1, which is -(1-[3-{(4-Pyridin-2-yl)piperazin-1-yl}]propyl)aminoisoquinoline.

16. A compound according to claim 1, which is -(1-[3-{(4-Pyridin-2-yl)piperazin-1-yl}]propyl)aminoisoquinoline hydrobromide.

17. A compound according to claim 1, which is 1(1-[3-{4-Phenylpiperazin-1-yl}]propyl)aminoisoquinoline.

18. A compound according to claim 1, which is 1-(1-[3-{4-Phenylpiperazin-1-yl}]propyl)aminoisoquinoline hydrobromide.

19. A compound according to claim 1, which is 1-(1-[3-{(4-[2,3-Dimethylphenyl])piperazin-1-yl}]propyl)aminoisoquinoline.

20. A compound according to claim 1, which is 1-(1-[3-{(4-[2,3-Dimethylphenyl])piperazin-1-yl}]propyl) aminoisoquinoline hydrobromide.

21. A compound according to claim 1, which is -(1-[2-{(4-[5-Fluoropyrimidin-2-yl])piperazin-1-yl}]ethyl) aminoisoquinoline.

22. A compound according to claim 1, which is -(1-[2-{(4-[5-Fluoropyrimidin-2-yl])piperazin-1-yl}]ethyl) aminoisoquinoline hydrobromide.

23. A compound according to claim 1, which is 1-(1-[4-{(4-[5-Fluoropyrimidin-2-yl])piperazin-1-yl}]butyl) aminoisoquinoline.

24. A compound according to claim 1, which is 1-(1-[4-{(4-[5-Fluoropyrimidin-2-yl])piperazin-1-yl}]butyl) aminoisoquinoline hydrobromide.

25. A compound according to claim 1, which is 1-(1-[4-{(4-[5-Methylpyrimidin-2-yl])piperazin-1-yl}]butyl) aminoisoquinoline.

26. A compound according to claim 1, which is 1-(1-[4-{(4-[5-Methylpyrimidin-2-yl])piperazin-1-yl}]butyl) aminoisoquinoline hydrobromide.

* * * * *